United States Patent [19]

Pavlin et al.

[11] Patent Number: 4,895,982
[45] Date of Patent: Jan. 23, 1990

[54] TRICARBOXYLIC ACIDS

[75] Inventors: Mark S. Pavlin, Lawrenceville, N.J.; Kathryn S. Hayes, Norristown, Pa.

[73] Assignee: Union Camp Corporation, Wayne, N.J.

[21] Appl. No.: 876,451

[22] Filed: Jun. 20, 1986

[51] Int. Cl.$^4$ ............................................. C07C 57/02
[52] U.S. Cl. ................................. 562/595; 260/407; 562/590; 530/230
[58] Field of Search ............. 260/407, 97.5; 562/595, 562/590

[56] References Cited

U.S. PATENT DOCUMENTS

| | | | |
|---|---|---|---|
| 2,793,219 | 5/1957 | Barrett et al. | 260/407 |
| 2,793,220 | 5/1957 | Barrett et al. | 260/407 |
| 3,076,003 | 1/1963 | Myers et al. | 260/407 |
| 3,100,784 | 8/1963 | Goebel | 260/407 |
| 3,412,039 | 11/1968 | Miller | 260/407 |

FOREIGN PATENT DOCUMENTS 904343  8/1962  United Kingdom ............... 260/407

Primary Examiner—Werren B. Lone
Attorney, Agent, or Firm—Edward J. Sites

[57] ABSTRACT

Tricarboxylic acids are prepared by reacting unsaturated mono- and dicarboxylic acids of specific carbon atom content in the presence of a catalytic proportion of an unactivated clay and water. The product acids of 34, 35, 36, 38, or 40 carbon atoms are useful as corrosion inhibitors, epoxy resins curing agents, lubricants, polymeric resin plasticizers and intermediates for synthetic polymeric resins.

10 Claims, 2 Drawing Sheets

TRICARBOXYLIC ACIDS

BACKGROUND OF THE INVENTION

1. Field of the Invention

The invention relates to mixtures of polymerized mono- and dicarboxylic acids and more particularly relates to tricarboxylic acids obtained from the reaction of unsaturated dicarboxylic acids containing 16, 17, 18, 20, or 22 carbon atoms or mixtures thereof with monocarboxylic acids containing 18 carbon atoms.

2. Brief Description of the Prior Art

It is well known that unsaturated fatty acids, particularly those derived from natural sources, are capable of being converted to dimer and trimer forms. This is usually realized by heating the unsaturated fatty acids in the presence of catalytic proportions of a mineral clay and, preferably, an acid-treated mineral clay, at temperatures in excess of about 180° C. with water under autogenous pressure. Representative of the prior art teachings are those found in the U.S. Pat. Nos. 2,793,219 and 2,793,220.

We have now discovered that unsaturated dicarboxylic acids having 16, 17, 18, 20, or 22 carbon acids, alone or in admixture, and monocarboxylic acids having 18 carbon atoms, will react with each other under the influence of clay catalysts to yield tricarboxylic acids of 34, 35, 36, 38 or 40 carbon atoms having unique and useful properties.

SUMMARY OF THE INVENTION

The invention comprises tricarboxylic acids obtained by reacting together an unsaturated dicarboxylic acid selected from the group consisting of those having 16, 17, 18, 20 and 22 carbon atoms, inclusive and an unsaturated monocarboxylic acid having 18 carbon atoms.

The acids of the invention are useful as corrosion inhibitors, epoxy resin curing agents, synthetic polymeric resin plasticizers and lubricants.

DETAILED DESCRIPTION OF THE PREFERRED EMBODIMENTS OF THE INVENTION

The method of the invention may be employed advantageously to react together a mixture of unsaturated mono- and dicarboxylic acids of the described carbon atom content, including mixtures of monounsaturated and polyunsaturated mono- and dicarboxylic acids. The products are crude mixtures which include some dicarboxylic acid dimer and some tetra-carboxylic acid dimer but comprise largely of unique tricarboxylic acids from the reaction of one molecule of monocarboxylic acid monomer and one molecule of dicarboxylic acid monomer. A wide variety of unsaturated dicarboxylic acids of the stated carbon content may be used to prepare the compositions of the invention. Exemplary of the unsaturated dicarboxylic acids used are:
hexadec-8-enedioic acid;
eicose-8,12-dienedioic acid;
7-vinyl-tetradecanedioic acid;
8-vinyl-octadec-10-enedioic acid;
8,13-dimethyleicose-8,12-dienedioic acid;
octadec-9-enedioic acid; and mixtures thereof.

Similarly, a wide variety of unsaturated monocarboxylic acids may be used to prepare compositions of the invention. Exemplary of unsaturated monocarboxylic acids used are:
linoleic acid (cis-9,cis-12-octadecadienoic acid);
oleic acid (cis-9-octadecenoic acid);
linolenic acid (cis-9,cis-12-octadecatrienoic acid);
elaidic acid (Trans-9-octadecenoic acid);
and mixtures thereof. Preferred are crude mixtures of fatty acids containing monocarboxylic acids such as are obtained from vegetable oils and tall oils, for example, soybean-derived fatty acids, and, most preferred, tall oil fatty acids.

The reaction is carried out by heating the acid reactants in the presence of a catalytic proportion of an unactivated clay catalyst. A catalytic proportion is generally within the range of from about 1 to about 10 percent by weight of the acid reactants.

The unactivated clay catalysts employed in the process of the invention are well known and commercially available. Representative of such clays are hectorite, montmorillonite, attapulgite, sepiolite and bentonite, per se or in combination with montmorillonite.

Advantageously employed in the reaction mixture is a modifying proportion of a catalyst modifier, i.e., an alkaline earth or alkali metal salt. Particularly advantageously, use of a lithium salt modifier effects the selectivity of the reaction and improves (reduces) coloration of the product acids. The proportion of catalyst modifier employed is generally within the range of from 0.5 to 6 milliequivalent per gram of clay catalyst employed.

Figure 1:
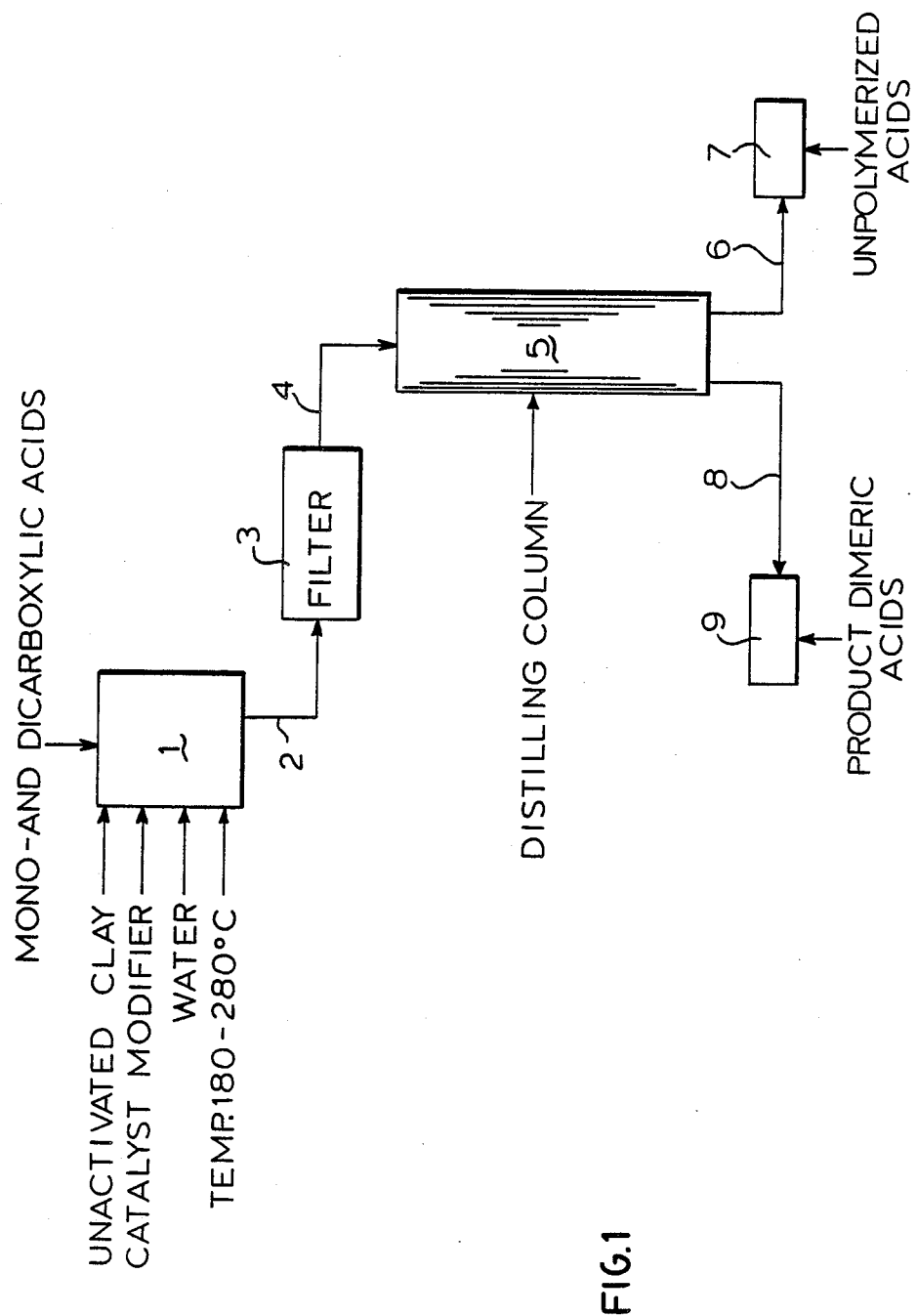
FIG. 1 is a schematic flow chart illustrating an embodiment method of the invention.

Referring now to the accompanying drawing of FIG. 1, a representative process of the invention will be described. As shown in the drawing, a suitable reactor vessel 1 is charged with $C_{18}$ monocarboxylic acid and dicarboxylic acids containing $C_{16}$, $C_{17}$, $C_{18}$, $C_{20}$ or $C_{22}$ carbon atoms, 1 to 10 percent by weight of an unactivated clay catalyst, and water (0.5–5 percent by weight of dicarboxylic acid). A modifying proportion of an alakali or alkaline earth metal salt may also be charged to vessel 1. The charge is heated to a temperature within the range of from 180° C. to 280° C. under autogenous pressures. The heating is continued until the mixture of acids has reacted. This usually requires a heating time of from about 2 to 5 hours; preferred conditions being about 4 hours at circa 245° C. The reaction mixture is then cooled to about 100° C. and about 1 weight percent of phosphoric acid is added. The resulting mixture is then stirred for 1 hour and the contents of the reactor vessel 1 are then discharged through a conduit line 2 into filter 3 and on through a conduit line 4 into a wiped film still 5 from which the residual unreacted acids are distilled. Distillation temperatures of 200°–300° C., at pressures of about 0.05–50 millimeters of mercury, are preferably maintained, but not especially critical. The line 6 is cooled and condensed into a receiver 7. The product acids are withdrawn through conduit line 8 into a receiving tank 9.

The following examples described the manner and process of making and using the invention and set forth the best mode contemplated by the inventor of carrying out the invention, but are not to be construed as limiting. Where given, acid numbers were determined by the method of ASTM D-1980 and viscosity by the method of ASTM D-446-74.

EXAMPLE 1

A charge of tall oil fatty acids* (150 gms) and $C_{20}$ dicarboxylic acids** (50 gms) was heated in an autoclave with 8 weight percent montmorillonite clay, a small amount of lithium carbonate to modify the clay, and 7 weight percent water at 260° C. for 3 hours. The crude product was then treated with phosphoric acid at about 100° C. and filtered. Monomeric material (63.7 g) was then removed by distillation of a portion of the crude acids on a Smith wiped-film molecular still to afford "dimeric" product as residue (65.7 g). An aliquot of this split product was analyzed by high pressure liquid chromatography, acid number and viscosity. The results are given in the Table below.

*Unitol AFL, containing 43.0% oleic, 33.6% linoleic, and 9.1% conjugated linoleic acids; Union Camp Corp., Wayne, N.J.
**ULB-20; OKAMURA OIL MILL, LTD., a mixture having the following composition:

| DIACID | % BY WEIGHT |
|---|---|
| $HOOC-(CH_2)_6-CH=CH-(CH_2)_6-COOH$ | 4–9% |
| $HOOC-(CH_2)_6-CH=CH-(CH_2)_2-CH=CH-(CH_2)_6-COOH$ | 35–52% |
| $HOOC-(CH_2)_5-CH(CH=CH_2)-(CH_2)_6-COOH$ | 2–4% |
| $HOOC-(CH_2)_6-CH(CH=CH_2)-CH_2-CH=CH-(CH_2)_6-COOH$ | 30–40% |

EXAMPLE 2

The procedure of Example 1 was followed except the proportions of the charge were changed in respect to 50 gms Unitol AFL, 150 gms ULB-20, and 6% clay. The product yields and properties are in the Table below.

EXAMPLE 3

Figure 2:
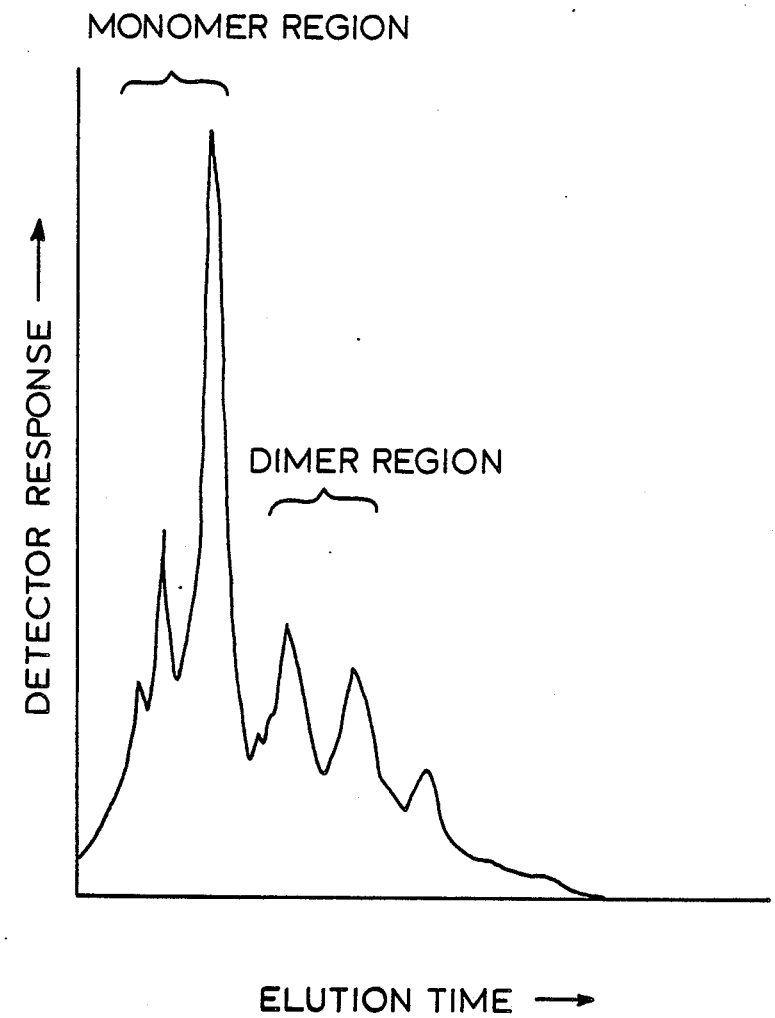
FIG. 2 is a high pressure liquid chromatograph obtained on an aliquot of the product prepared in Example 3, infra.

The procedure of Example 1 was followed except the proportions of the charge were changed in respect to 100 gms each of Unitol AFL and ULB-20, and 4% clay and the reaction was conducted at 245° C. The product yield and properties are in the Table below. The liquid chromatograph of the crude product (FIG. 2) clearly shows two types of polycarboxylic acids in the "dimer" region, of roughly equal amount.

TABLE
Product Acids - Yields and Properties

|  | Example 1 | Example 2 | Example 3 |
|---|---|---|---|
| % Product Acids Split | 51 | 56 | 60 |
| % Monomer in Product | 0 | 5 | 18 |
| Acid Number* | 226 | 285 | 270 |
| Peak Molecular Weight≠ (by HPLC) | 528 | 583 | — |
| Viscosity (75° C., cps) | 855 | 3350 | 1345 |
| Viscosity (100° C., cps) | 173 | 518 | 305 |

*Theoretical acid number for a $C_{38}$-tricarboxylic acid is 272.
≠Theoretical molecular weight for a $C_{38}$-tricarboxylic acid is 620.

What is claimed is:

1. Tricarboxylic acids having 34, 35, 36, 38 or 40 carbon atoms prepared by:
   providing a mixture of acids which comprises an unsaturated dicarboxylic acid selected from the group consisting of unsaturated dicarboxylic acids having 16, 17, 18, 20 or 22 carbon atoms and an unsaturated monocarboxylic acid having 18 carbon atoms;
   heating the acid mixture to a temperature of from 180° C. to 280° C. in the presence of a catalytic proportion of an unactivated clay, from 0.5 to 6 milliequivalent per gram of clay catalyst of a compound selected from the group consisting of an alkali or alkaline earth metal salt, and 0.05 to 5 percent by weight of acid of water.

2. Acids of claim 1 wherein the dicarboxylic acid comprises linear and/or branched diendioic acids having 20 carbon atoms.

3. Acids of claim 1 wherin the dicarboxylic acid comprises eicose-8,12-dienedioic acid or 8-vinyl-octadec-10-enedioic acid.

4. Acids of claim 1 wherein the dicarboxylic acid comprises 8,13-dimethyleicose-8,12-dienedioic acid.

5. Acids of claim 1 wherein the dicarboxylic acid comprises hexadec-8-enedioic acid or 7-vinyl-tetradecanedioic acid.

6. Acids of claim 1 wherein the dicarboxylic acid comprises octadec-9-enedioic acid.

7. Acids of claim 1 wherein the monocarboxylic acid comprises a mixture of oleic and linoleic acids.

8. Acids of claim 1 wherein the unactivated clay is montmorillonite.

9. Acids of claim 1 wherein the modifying salt is lithium carbonate.

10. Acids of claim 1 wherein the modifying salt is lithium hydroxide.

* * * * *